United States Patent [19]

Bauer et al.

[11] Patent Number: 4,702,464
[45] Date of Patent: Oct. 27, 1987

[54] GUIDE DEVICE FOR GUIDING A MOVABLE PART OF AN APPARATUS RELATIVE TO A FIXED PART OF THE APPARATUS

[75] Inventors: Ludwig Bauer, Schriesheim; Erwin Schneider; Walter Rensch, both of Nussloch; Helmut Weinhold, Ketsch, all of Fed. Rep. of Germany

[73] Assignee: Cambridge Instruments GmbH, Fed. Rep. of Germany

[21] Appl. No.: 762,184

[22] Filed: Aug. 5, 1985

[30] Foreign Application Priority Data

Aug. 22, 1984 [DE]  Fed. Rep. of Germany ....... 3430821
Sep. 12, 1984 [DE]  Fed. Rep. of Germany ....... 3433460

[51] Int. Cl.$^4$ .............................................. B26D 7/06
[52] U.S. Cl. ..................................... 269/55; 269/285; 83/915.5
[58] Field of Search ...................... 83/915.5, 410, 703; 308/3 A; 269/55, 285, 58

[56] References Cited

U.S. PATENT DOCUMENTS

| 2,822,726 | 2/1958 | Blum | 83/915.5 |
| 3,460,417 | 8/1969 | Johnson | 83/915.5 |
| 3,564,961 | 2/1971 | Burkhardt | 83/915.5 |
| 3,799,029 | 3/1974 | Cole et al. | 83/915.5 |
| 3,828,641 | 8/1974 | Sitte | 83/915.5 |

Primary Examiner—Robert C. Watson
Attorney, Agent, or Firm—Alan H. Spencer

[57] ABSTRACT

A guide device for guiding a movable part of an apparatus relative to a fixed part of the apparatus, includes a first guide rail adapted to be provided on the movable part and a second guide rail adapted to be provided on the fixed part. Bearing means comprising a plurality of roller elements disposed in a roller support is disposed in a longitudinal groove between the first and second guides and movable relative thereto. Biasing means is provided which biases the bearing means toward a predetermined position.

8 Claims, 3 Drawing Figures

GUIDE DEVICE FOR GUIDING A MOVABLE PART OF AN APPARATUS RELATIVE TO A FIXED PART OF THE APPARATUS

BACKGROUND OF THE INVENTION

This invention relates to a guide device for guiding a movable part of an apparatus relative to a fixed part of the apparatus.

Guide devices taking the form of ball guides or of cross-roller guides have been used for some time to guide a movable part of an apparatus linearly relative to a fixed part of the apparatus. Such guide devices often comprise two parallel guide rails one of which is arranged on the movable part and the other of which is arranged on the fixed part. Each guide rail is provided with a longitudinal groove and a plurality of roller elements arranged in a cage are movable linearly between the two guide rails in the grooves. End stops are usually provided on the guide rails to limit movement of the cage.

A field of use of guide devices of this type is that of the linear guidance of specimen clamping means in microtomes. In this case the movable part comprises the specimen clamping means while the fixed part comprises a base part of the microtome or a housing of the microtome.

In rotary microtomes the specimen clamping means is usually guided by the guide device so as to be movable vertically upwardly and downwardly.

In another kind of microtome, the specimen clamping means is guided by the guide device forwardly and rearwrdly in the horizontal direction. Even after a plurality of forward and rearward movement, which may occur at a high speed, the cage with the roller elements is not biased towards any particular position on the guide rails.

In contrast to this, in rotary microtomes the force of gravity draws the cage and the roller elements downwardly. This downward movement of the cage and roller elements depends upon the number of vertical load cycles, i.e. the number of up-and-down movements of the specimen clamping means; it also depends upon the number of vertical strokes made per unit of time.

When the cage rests against the lower end stop after a long period of use, the guidance properties of the guide device are impaired. Normally the cage should be located centrally between the end stops on the guide rails, because the best possible guidance properties can only be obtained when the cage is in this central position.

SUMMARY OF THE INVENTION

An object of the present invention is to provide an improved guide device which overcomes the aforementioned problems.

According to one aspect of the present invention there is provided a guide device for guiding a movable part of an apparatus relative to a fixed part of the apparatus, comprising a first guide adapted to be provided on the movable part, a second guide adapted to be provided on the fixed part, bearing means disposed between the first and second guides and movable relative thereto, and biasing means adapted to bias the bearing means towards a predetermined position.

Advantageously the first and second guides each comprises a guide rail having a longitudinal groove, the guide rail of each guide being arranged substantially parallel to one another.

Preferably the bearing means comprises a plurality of roller elements arranged within a roller support, said roller elements and roller support being movable linearly between the guide rails.

Stop means may be provided on the guide rails to limit movement of the roller elements and roller support.

Desirably the biasing means comprises an elastically resilient member disposed between the roller support and the fixed part of the apparatus. The particular advantage of using an elastically resilient member is that its spring force is linearly dependent on its deformation; this deformation depends on the displacement of the roller support and roller elements from the determined position. Hence, in the event of a relatively large displacement, the restoring force of the resilient member is greater. In this way, when the roller support and roller elements are displaced from the predetermined position they are returned to the predetermined position with a restoring force having a magnitude which increases with increasing displacement from the predetermined position.

Preferably the resilient member is dimensioned such that when the bearing means is in the predetermined position the resilient member is tensioned by means of a spring force which is equal to the force due to the weight of the bearing means. Such a dimensioning of the resilient member achieves the particular advantage that the roller support and roller elements are always biased towards the predetermined position. Thus, when the roller support and roller elements are in a position above the predetermined position, the spring force directed upwardly is less than the weight of the roller support and the roller elements, so that the support and the elements are drawn downwardly to the predetermined position under the influence of gravity. This restoring force increases with increasing upward displacement of the support and roller elements, because when the displacement is greater the spring force of the elastically resilient member decreases linearly until it becomes substantially zero at a displacement corresponding to the upper end position of the support and roller elements.

Conversely, the restoring spring force becomes greater, with increasing displacement of the support and roller elements below the predetermined position.

The resilient member may be a tension spring. It is possible to arrange the tension spring between an upper end region of the cage and the fixed part of the apparatus. However, it is preferred to arrange the tension spring between a lower end region of the roller support and the fixed part, because this results in a smaller overall construction height of the guide device.

The resilient member may alternatively comprise a compression spring which is located between the upper end region of the roller support and the fixed part of the apparatus.

It is preferred to use tension springs rather than compression springs because they can be provided with a more accurate spring constant than compression springs. In either case, it is important that the spring constant is selected so that the spring force of the resilient member corresponds exactly to the weight of the roller support and the roller elements when they are in in the predetermined position.

Alternatively, the elastically resilient member can be dimensioned such that in the uppermost position of the roller support and roller elements the elastically resilient member is relaxed, and in the lowermost position it is tensioned with the spring force which corresponds at least approximately to double the total weight of the roller support and the roller elements. This construction results in the predetermined position lying at a position substantially midway along the length of the guides.

In another embodiment the resilient member may be a tension spring which is disposed between the fixed part of the apparatus and an elongate element such as a band or a wire which is secured to an upper end region of the roller support, and a deflecting roller is provided around which the elongate element is deflected. Such an arrangement of the resilient member is advantageous when the space available for the resilient member is relatively small. An elongate element such as a band or wire may have sufficient space even if there is not enough space for the resilient member; certain types of resilient member, for example a helical spring, may require more space than is available in the region of the roller support. The deflecting roller can be arranged at any location, even at a relatively long distance from the roller support.

In a further embodiment the biasing means comprises a counterweight and an elongate element (such as a band or wire) having front and rear ends, the rear end being secured to the counterweight and the front end being secured to an upper end region of the roller support, and a deflecting roller is provided around which the elongate element is deflected.

Preferably the predetermined position is adjustable. This may be achieved by providing means to adjust the position at which the biasing means is secured to the fixed part of the apparatus.

An advantge of the guide device according to the invention is that even after a large number of vertical upward and downward strokes, the bearing means does not tend to move in a downward direction under the influence of gravity. This prevents the guides from being worn on one side only, and prevents the consequent impairment of the guidance properties.

In the guide device according to the invention the predetermined position is ideally arranged to be disposed centrally of the length of the guides, (i.e. substantially midway along the length of the guides) so that the support rollers and the roller elements are always biased back to the central position whenever the bearing means has moved out of this position.

The guide device according to the invention at all times guarantees excellent guidance properties for guiding a movable part relative to a fixed part, and is especially useful for vertical guidance. The guide device according to the invention is especially suitable or use in apparatus which executes a plurality of vertical load cycles and a large number of strokes per unit time. Examples of such an apparatus include a machine tool with a support movable up and down vertically, and an optical device.

According to another aspect of the invention there is provided a rotary microtome comprising a housing, specimen clamping means movable relative to the housing, a first guide disposed on the housing, a second guide disposed on the specimen clamping means, bearing means disposed between the first and second guides and movable relative thereto, and biasing means adapted to bias the bearing means towards a predetermined position.

The first and second guides, the bearing means and the biasing means may be the same as described above.

Typically the guides are arranged vertically so that the specimen clamping means executes a vertical upward and downward movement. The predetermined position is ideally arranged to be disposed substantially centrally of the length of the guides.

BRIEF DESCRIPTION OF THE DRAWINGS

Reference is now made to the accompanying drawings in which.

DESCRIPTION OF THE PREFERRED EMBODIMENTS

Figure 1:
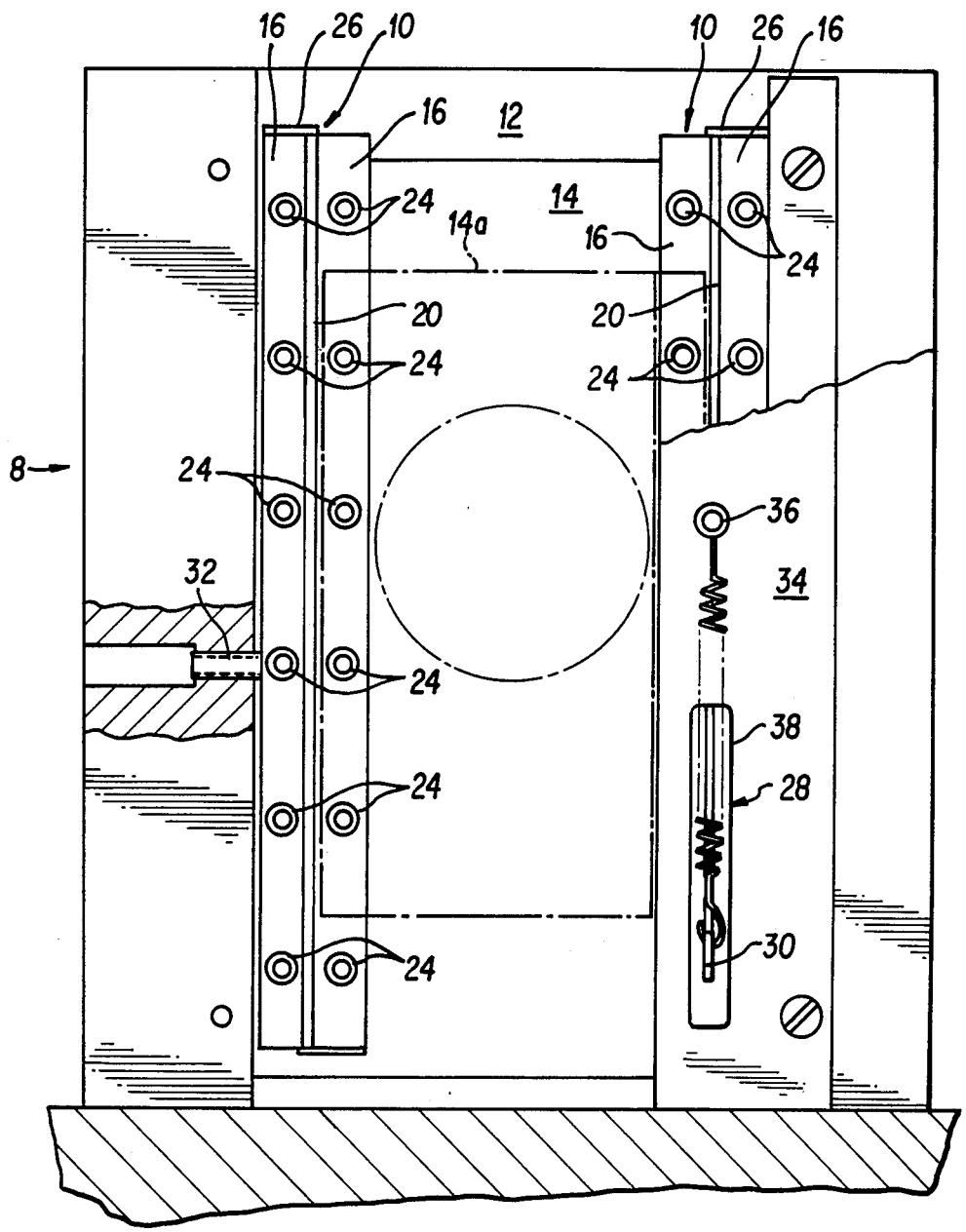
FIG. 1 is a front elevation partly in section of a rotary microtome having a guide device according to the invention.
Figure 2:
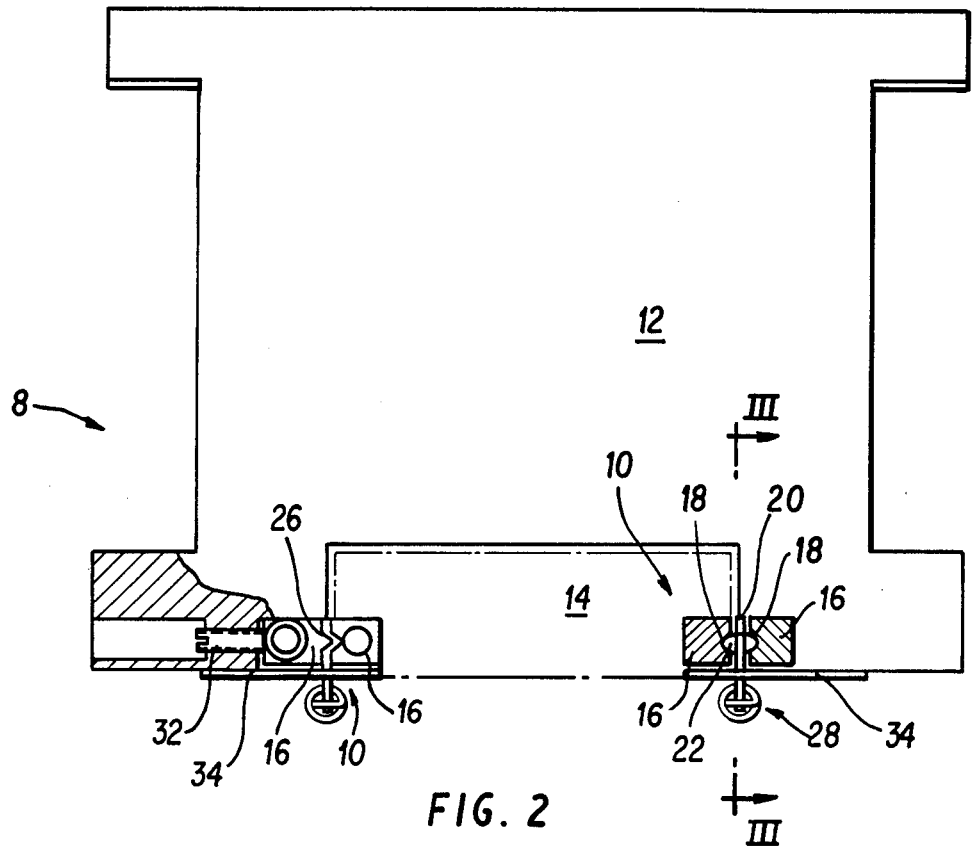
FIG. 2 is a plan view partly in section of the rotary microtome shown in FIG. 1 in the direction II.

FIGS. 1 and 2 show apparatus comprising a rotary microtome generally designated 8 having a fixed housing 12 and specimen clamping means 14. The specimen clamping means 14 is movable upwardly and downwardly relative to the housing 12. The microtome 8 is provided with a guide device comprising a cross roller guide 10, bearing means in the form of a roller support 20 and roller elements 22, and biasing means 28.

Two of said cross roller guides 10 are arranged for guiding the vertical movement of the specimen clamping means 14 relative to the housing 12. Each cross roller guide 10 comprises two guides in the form of guide rails 16 arranged parallel next to one another; each guide rail 16 is provided with a longitudinal groove 18.

The roller support 20 comprises a cage which is disposed between each pair of guide rails 16 in the longitudinal grooves 18. The roller elements 22 comprise cylindrical rollers which are juxtaposed within the cage 20.

One of each pair of the guide rails 16 is secured to the housing 12 by means of screws 24; the other of the guide rails 16 is secured to the specimen clamping means 14 also by screws 24.

Stop means in the form of end stops 26 are screwed to the guide rails 16 to limit the stroke of the cage 20. The end stops 26 also aid in the assembly of the guide device.

A carriage 14a is provided (shown in ghost lines) for holding a specimen arm and for moving the arm together with a specimen in a direction normal to the plane of FIG. 1.

Each cage 20 is provided with biasing means 28 for biasing the cage 20 and the rollers 22 towards a predetermined position. In the embodiment shown, the predetermined position is a position disposed substantially centrally of the length of the guide rails 16, in which position optimum guidance of the specimen clamping means 14 relative to the housing 12 is obtained.

The biasing means 28 comprises an elastically resilient member, such as a tension spring. The biasing means 28 is disposed between the roller cage 20 and the housing 12, and is dimensioned such that in the predetermined position it is tensioned with a spring force which corresponds to the total weight of the cage 20 and the rollers 22.

The biasing means 28 is secured to a lower end region 30 of the cage 20 and to the housing 12.

When the guide device is assembled, the cage 20 is first arranged in such a way that it is at the same distance from each of the end stops 26 on each guide rail 16. Each cross roller guide 10 is subsequently adjusted free of play by means of set screws 32, so that the rollers 22 can roll in the longitudinal grooves 18 during the vertical movement of the guide rail 16 which is connected to the specimen clamping means 14.

A considerable advantage of the guide device according to the invention is that it can be incorporated in an existing rotary microtome. For this purpose, the cover plates on the existing microtome can be replaced with modified cover plates 34 having a projection 36 and a longitudinal slot 38. The biasing means 28 is suspended between the projection 36 of the cover plate 34 and the lower end region 30 of the cage 20. The region 30 of the roller cage 20 is hook-shaped as shown in FIG. 3, and is provided with an aperture 31 through which the biasing means 28 extends to secure the biasing means to the end region 30.

Figure 3:
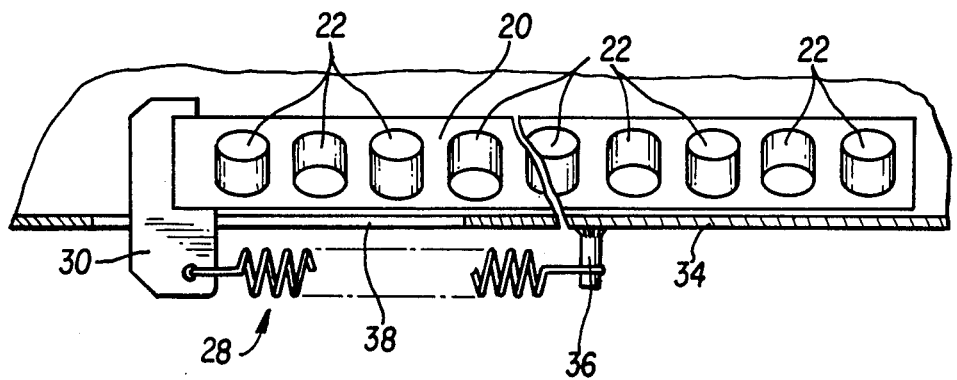
FIG. 3 is a view on lines III—III of FIG. 2.

FIG. 3 shows the roller cage 20 with the cylindrical rollers 22, and the cover plate 34 with the elongate slot 38 through which the lower end region 30 of the cage 20 extends.

For the accurate adjustment of the biasing means the projection 36 can be made adjustable and lockable relative to the housing 12.

We claim:
1. A rotary microtome comprising
  a housing,
  specimen clamping means movable relative to the housing,
  a first guide disposed on the housing,
  a second guide disposed on the specimen clamping means,
  bearing means disposed between the first and second guides and movable relative thereto, and
  biasing means adapted to bias the bearing means towards a predetermined position.
2. A rotary microtome according to claim 11 wherein the first and second guides each comprises a guide rail having a longitudinal groove, said guide rails being arranged substantially parallel to one another.
3. A rotary microtome according to claim 11 wherein the bearing means comprises a plurality of roller elements arranged within a roller support, said roller elements and roller support being movable linearly between the guide rails.
4. A rotary microtome according to claim 3 wherein stop means is provided on the guide rails to limit movement of the roller elements and roller supports.
5. A rotary microtome according to claim 3 wherein the biasing means comprises an elastically resilient member disposed between the roller support and the housing.
6. A rotary microtome according to claim 5 wherein the resilient member is spring dimensioned such that when the bearing means is in the predetermined position the spring is tensioned by means of a force which is equal to the force due to the weight of the bearing means.
7. A rotary microtome according to claim 5 wherein the resilient member is a tension spring which is disposed between a lower end region of the roller support and the housing.
8. A rotary microtome according to claim 5 wherein the resilient member is a tension spring which is disposed between the housing and an elongate element secured to an upper end region of the roller support.

* * * * *